US00PP37448P2

(12) United States Plant Patent
Shafer

(10) Patent No.: US PP37,448 P2
(45) Date of Patent: May 26, 2026

(54) ***SALVIA* PLANT NAMED 'Balmyslue'**

(50) Latin Name: *Salvia farinacea*
Varietal Denomination: Balmyslue

(71) Applicant: Ball Horticultural Company, West Chicago, IL (US)

(72) Inventor: Gail Shafer, Santa Maria, CA (US)

( * ) Notice: Subject to any disclaimer, the term of this patent is extended or adjusted under 35 U.S.C. 154(b) by 0 days.

(21) Appl. No.: 19/350,047

(22) Filed: Oct. 5, 2025

(51) Int. Cl.
*A01H 5/02* (2018.01)
*A01H 6/50* (2018.01)

(52) U.S. Cl.
USPC ..... Plt./475

(58) Field of Classification Search
None
See application file for complete search history.

(56) References Cited

U.S. PATENT DOCUMENTS

PP29,605 P2 * 8/2018 Trees ..... Plt./475

* cited by examiner

*Primary Examiner* — Susan Mccormick Ewoldt
(74) *Attorney, Agent, or Firm* — Megan Bowman

(57) ABSTRACT

A new and distinct cultivar of *Salvia* plant named 'Balmyslue', characterized by its dark violet-colored flowers, green-colored foliage, and compact, upright growth habit, is disclosed.

1 Drawing Sheet

Latin name of genus and species of plant claimed: *Salvia farinacea.*

Variety denomination: 'Balmyslue'.

BACKGROUND OF THE INVENTION

The present invention relates to a new and distinct cultivar of *Salvia* plant botanically known as *Salvia farinacea* and hereinafter referred to by the cultivar name 'Balmyslue'.

The new cultivar originated in a controlled breeding program in Arroyo Grande, California during October 2015. The objective of the breeding program was the development of *Salvia* cultivars having large flowers with attraction coloration, and a compact, medium-upright growth habit.

The new *Salvia* cultivar is the result of self-pollination of Sallyfun 'Blue Ocean', not patented, characterized by its medium, blue-colored flowers, medium, green-colored foliage, and low vigor, upright growth habit. The new cultivar was discovered and selected as a single flowering plant within the progeny of the above stated self-pollination during September 2020 in a controlled environment in Arroyo Grande, California.

Asexual reproduction of the new cultivar by terminal stem cuttings since September 2020 in Arroyo Grande, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmyslue' as a new and distinct cultivar of *Salvia* plant:

1. Dark violet-colored flowers;
2. Dark, green-colored foliage; and
3. Compact, upright growth habit.

Plants of the new cultivar differ from plants of the female parent primarily by flowering earlier and having more branches per plant.

Of the many commercially available *Salvia* cultivars, the most similar in comparison to the new cultivar is *Salvia* Mysty 'Balsalmysty', U.S. Plant Pat. No. 29,605. However, in side-by-side comparisons, plants of the new cultivar differ from plants of 'Balsalmysty' in at least the following characteristics:

1. Plants of the new cultivar have shorter and narrower flower spikes than plants of 'Balsalmysty'; and
2. Plants of the new cultivar have more branches per plant than plants of 'Balsalmysty '.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balmyslue'. The plants were approximately 3.5 months old and grown in 6-inch pots for approximately 8 weeks in a greenhouse in West Chicago, Illinois. Plants were given one pinch three weeks before transplant.

DETAILED BOTANICAL DESCRIPTION

Figure 1:
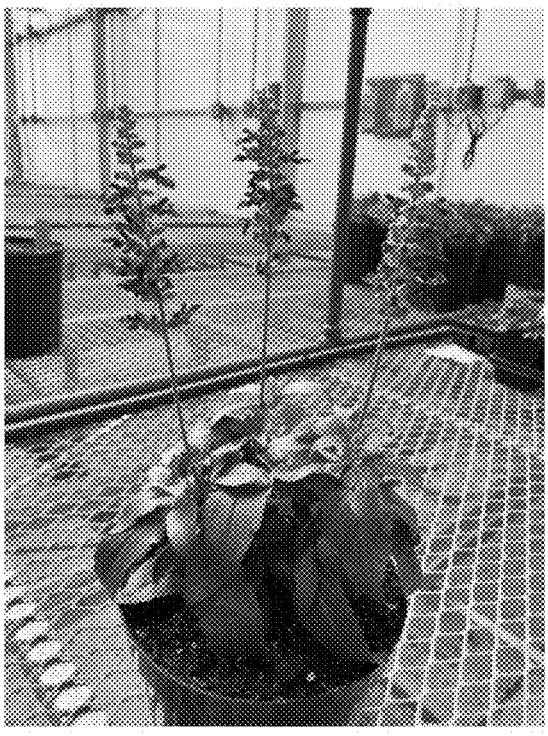
FIG. 1 illustrates a side view of the overall growth and flowering habit of 'Balmyslue'.
Figure 2:
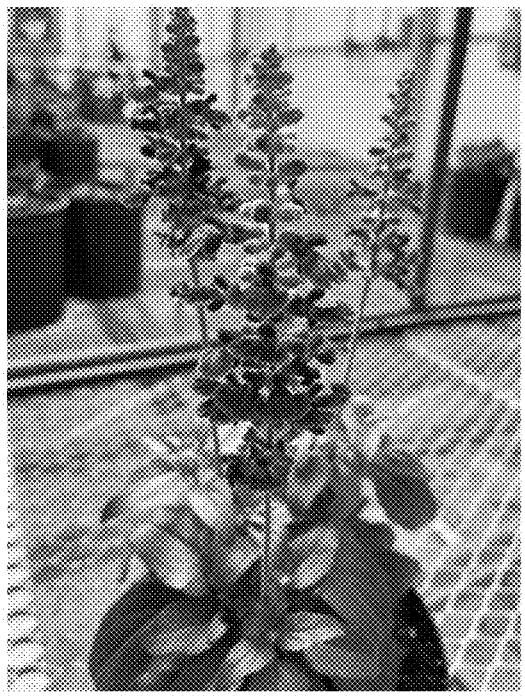
FIG. 2 illustrates a close-up view of an inflorescence of 'Balmyslue'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2025 under natural light conditions in West Chicago, Illinois.

The following descriptions and measurements describe approximately 3.5-month-old plants produced from cuttings from stock plants and grown in a double polyethylene under conditions comparable to those used in commercial practice. The plants were grown in West Chicago, Illinois in 6-inch pots for approximately 5 weeks utilizing a soilless growth medium. Plants were pinched three weeks before transplant. Greenhouse temperatures were maintained at approximately 65° F. to 70° F. (18.3° C. to 21.1° C.) during the day and approximately 60° F. to 65° F. (15.6° C. to 18.3° C.) during the night. Supplemental lighting was used. Measurements and numerical values represent averages of typical plants.

Botanical classification: *Salvia farinacea* 'Balmyslue'.

Parentage:

*Female and male parents*.—Sallyfun 'Blue Ocean', not patented.

Propagation:

*Type cutting*.—Terminal stem.

*Time to initiate roots*.—Approximately 6 to 9 days.

*Time to produce a rooted cutting*.—Approximately 21 to 35 days.

*Root description*.—Medium thickness, fibrous, brown in color.

*Rooting habit*.—Freely branching.

Plant description:

*Commercial crop time*.—Approximately 6 to 10 weeks from a rooted cutting to finish in a 15 cm pot.

*Growth habit and general appearance*.—Compact, medium growth habit.

*Size*.—Height from soil level to top of plant plane: Approximately 27.0 cm. Width: Approximately 20.0 cm.

*Branching habit*.—Freely branching. Pinching enhances lateral branching. Quantity of branches per plant: Approximately 2 main basal branches and approximately 3-4 lateral branches.

*Branch*.—Shape: Square in cross section. Strength: Strong. Length to base of inflorescence: Approximately 16.0 cm. Diameter: Approximately 4.0 mm. Length of central internode: Approximately 3.5 cm. Texture: densely pubescent. Color of young and mature stems: 143B.

Foliage description:

*General description*.—Quantity of leaves per main branch: Approximately 14. Fragrance: Light, sage-like. Form: Simple. Arrangement: Opposite.

*Leaves*.—Aspect: Acute to perpendicular angle to stem. Shape: Lanceolate. Margin: Crenate. Apex: Acute. Base: Oblique. Venation pattern: Pinnate. Length of mature leaf: Approximately 7.0 cm. Width of mature leaf: Approximately 2.5-4.0 cm. Texture of upper surface: smooth, sparsely pubescent. Texture of lower surface: Smooth, densely pubescent along venation. Color of upper surface of young foliage: 137C and venation of 147B. Color of lower surface of young foliage: Closest to 137D with venation of 145B. Color of upper surface of mature foliage: 137A and venation of 145B. Color of lower surface of mature foliage: 137C with venation of 146C.

*Petiole*.—Length: Approximately 1.5 cm. Diameter: Approximately 2.0 mm. Texture: Moderately pubescent. Color: 146C.

Flowering description:

*Flowering habit*.—'Balmyslue' is freely flowering under outdoor growing conditions with substantially continuous blooming from spring through autumn and year-round in greenhouse environment.

*Lastingness of individual floret*.—Approximately 4 to 5 days.

Inflorescence description:

*General description*.—Type: Spikes in verticillaster arrangement, florets in clusters of six, not persistent. Quantity of inflorescences per plant: Approximately 12. Fragrance: Faint, sweet. Length or height of inflorescence: Approximately 15.0-20.0 cm. Width of inflorescence: Approximately 3.5 cm. Quantity of fully open flowers per inflorescence: Approximately 12.

*Peduncle*.—Shape: Square in cross section. Strength: Strong. Aspect: Erect. Length: Approximately 5.0 cm. Diameter: Approximately 2.0 mm. Texture: Densely glandular pubescent. Color: 146B.

Flower description:

*Type*.—Single, zygomorphic.

*Bud*.—Rate of opening: Generally, takes 2 to 3 days for bud to progress from first color to fully open flower.

*Bud just before opening*.—Shape: Obovoid. Length: Approximately 0.8 cm. Diameter: Approximately 3.0 mm. Texture: Moderately pubescent. Color: Calyx of N92B and petals of 90B.

*Corolla*.—Shape: Bilabiate, lower lip having three lobes, base fused. Width: Approximately 0.8 cm. Length: Approximately 1.5 cm. Depth: Approximately 1.0 cm.

*Upper lip*.—Shape: Hooded. Margin: Entire. Apex: Rounded. Length from throat: Approximately 5.0 mm. Width: Approximately 3.0 mm. Texture of inner surface: Glabrous. Texture of outer surface: Densely pubescent. Color of pubescence: N89B. Color of inner surface when first and fully open: N88C. Color of outer surface when first and fully open: N88A.

*Lower lip*.—Shape of central lobe: Obovate. Margin: Entire. Apex of central lobe: Emarginate. Apex of lateral lobes: Rounded. Length from throat of central lobe: Approximately 1.1 cm. Width of central lobe: Approximately 1.0 cm. Length from throat of lateral lobes: Approximately 5.0 mm. Width of lateral lobes: Approximately 3.0 mm. Texture of upper surface: Glabrous. Texture of lower surface: Sparsely pubescent. Color of upper surface when first and fully open: N89C with central streaks of 85D. Color of lower surface when first and fully open: 91C with N88A near margins.

*Corolla tube*.—Length: Approximately 8.0 mm. Diameter at opening: Approximately 2.0 mm. Diameter at base: Approximately 1.0 mm. Texture of inner and outer surfaces: Glabrous. Color of inner surface when first and fully open: 91C. Color of outer surface when first and fully open: 91C.

*Calyx*.—Shape: Tubular. Length: Approximately 6.0 mm. Diameter: Approximately 4.0 mm.

*Sepals*.—Quantity per flower: Fused into two lobes. Shape: Obovate. Apex: Upper lobe acute, lower lobe notched. Length: Approximately 6.0 mm. Width of lobes: Approximately 4.0 mm. Texture of inner surface: Glabrous. Texture of outer surface: Densely pubescent. Color of inner surface: 144B. Color of outer surface: 138A with N88A at apex, color appears lighter due to pubescence.

*Bracts*.—Quantity: Two bracts located at the base of each floret cluster. Length: Approximately 5.0 mm. Width: Approximately 5.0 mm. Texture of inner surface: Glabrous. Texture of outer surface: Densely pubescent. Color of inner surface: 144A. Color of outer surface: 138A, color appears lighter due to pubescence

*Pedicel*.—Strength: Strong, flexible. Aspect: At an acute angle. Length: Approximately 1.0 mm. Diameter: Approximately 0.5 mm. Texture: Densely pubescent. Color: 138A, color appears lighter due to pubescence.

*Reproductive organs*.—Androecium: Stamen quantity: 2 per flower, dorsifixed, strongly curved. Stamen length: Approximately 0.7 cm. Filament length: Approximately 0.5 cm. Filament color: NN155D with lower half of 86A. Anther shape: Oblong. Anther length: Approximately 1.5 mm. Anther color: N89A. Pollen amount: Abundant. Pollen color: 14A. Gynoecium: Pistil quantity: 1 per flower, slightly curved. Pistil length: Approximately 1.0 cm. Stigma shape: Cleft, two-parted. Stigma length: 3.0 mm. Stigma color: N89A. Style length: Approximately 3.0 cm. Style color: 91D. Style texture: Glabrous. Ovary length: Approximately 1.0 mm. Ovary color: 1D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balmyslue', substantially as herein illustrated and described.

* * * * *